ABSTRACT

United States Patent [19]
Mangold et al.

[11] 3,966,750
[45] June 29, 1976

[54] N-3,5-DICHLOROPHENYLOXAZALIDINES

[75] Inventors: Dietrich Mangold, Neckargemuend; Bernd Zeeh, Ludwigshafen; Ernst-Heinrich Pommer, Limburgerhof, all of Germany

[73] Assignee: BASF Aktiengesellschaft, Ludwigshafen (Rhine), Germany

[22] Filed: May 28, 1974

[21] Appl. No.: 473,505

[52] U.S. Cl. .............................. 260/307 B; 424/272
[51] Int. Cl.² ........................................ C07D 263/44
[58] Field of Search ............................. 260/307 B

[56] References Cited
UNITED STATES PATENTS 3,709,895   1/1973   Kohlhaupt et al. ............... 260/307 B

FOREIGN PATENTS OR APPLICATIONS 79,984   8/1963   France
2,207,576   8/1973   Germany

OTHER PUBLICATIONS

Coelln et al., C.A. 76, 82178v, (1972).

*Primary Examiner*—Raymond V. Rush
*Attorney, Agent, or Firm*—Johnston, Keil, Thompson & Shurtleff

[57] ABSTRACT

N-(3,5-dichlorophenyl)-5-H or lower alkyl-5-lower alkenyloxazolidine-2,4-diones or N-(3,5-dichlorophenyl)-5-methyleneoxazolidine-2,4-dione and fungicidal uses thereof.

1 Claim, No Drawings

N-3,5-DICHLOROPHENYLOXAZALIDINES

The present invention relates to new and valuable oxazolidine derivatives having good fungicidal properties; fungicides containing these compounds as active ingredients; and the use of these compounds as fungicides.

It is known that N-3,5-dichlorophenyloxazolidines, e.g. N-3,5-dichlorophenyl-5,5-dimethyloxazolidine-2,4-dione, may be used as fungicides. However, they only have a poor fungicidal action.

We have now found that oxazolidine derivatives of the formula

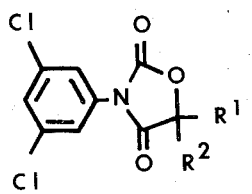

where $R^1$ and $R^2$ are identical or different and each denotes haloalkenyl or alkenyl, $R^1$ additionally denotes hydrogen or alkyl of 1 to 4 carbon atoms, or $R^1$ and $R^2$ together denote methylene, have a good fungicidal action which is superior to that of prior art compounds.

Examples of compounds according to the invention are as follows:

N-(3,5-dichlorophenyl)-5-methyl-5-(1-bromovinyl)-oxazolidine-2,4-dione;

N-(3,5-dichlorophenyl)-5-methyl-5-(2-bromo-propenyl)-2,4-oxazolidinedione;

N-(3,5-dichlorophenyl)-5-(3-bromopropen-1-yl)-2,4-oxazolidinedione;

N-(3,5-dichlorophenyl)-5-methyl-5-vinyloxazolidine-2,4-dione;

N-(3,5-dichlorophenyl)-5-methyl-5-propenyloxazolidine-2,4-dione;

N-(3,5-dichlorophenyl)-5-methyl-5-(2,2-dimethyl-vinyl)-oxazolidone-2,4-dione;

N-(3,5-dichlorophenyl)-5-propenyl-5-vinyloxazolidine-2,4-dione;

N-(3,5-dichlorophenyl)-5-methyleneoxazolidine-2,4-dione, m.p. 141°C.

The new compounds have a very good action on phytopathogenic fungi and on the following fungi which destroy industrial products such as textiles, surface coatings and materials containing cellulose:

*Erysiphe graminis*
*Erysiphe cichoriacearum*
*Botrytis cinerea*
*Monilia fructigena*
*Piricularia oryzae*
*Pellicularia filamentosa*
*Sclerotinia sclerotiorum*
*Aspergillus niger*
*Chaetomium globosum.*

The compounds are particularly suitable for preventing and curing plant diseases caused by fungi.

The agents according to the invention may be used as solutions, emulsions, suspensions or dusts. The form of application depends entirely on the purpose for which the agents are being used; in any case it should ensure a fine distribution of the active ingredient.

For the preparation of solutions to be sprayed direct, hydrocarbons having boiling points higher than 150°C, e.g. tetrahydronaphthalene or alkylated naphthalene, or organic liquids having boiling points higher than 150°C and having one or more than one functional group, e.g. the keto group, the ether group, the ester group or the amide group, this group or these groups being attached as substituent(s) to a hydrocarbon chain or being a component of a heterocyclic ring, may be used as spray liquids.

Aqueous formulations may be prepared from emulsion concentrates, pastes or wettable powders by adding water. To prepare emulsions the ingredients as such or dissolved in a solvent may be homogenized in water or organic solvents by means of wetting or dispersing agents, e.g. polyethylene oxide adducts. Concentrates which are suitable for dilution with water may be prepared from active ingredient, emulsifying or dispersing agent and possibly solvent.

Dusts may be prepared by mixing or grinding the active ingredients with a solid carrier, e.g. kieselguhr, talc, clay or fertilizers The preparation of the compounds and their use are illustrated in the following examples.

The active ingredients may also be mixed with a fungicide, insecticide, herbicide, growth regulator or soil disinfectant.

EXAMPLE 1

N-3,5-dichlorophenyl-5-methyl-5-vinyloxazolidinedione 35 parts of 3,5-dichlorophenyl isocyanate, 26 parts of ethyl vinyl lactate and 5 parts of triethylamine in 600 parts of benzene are kept under reflux for 6 hours in a stirred apparatus. After the reaction mixture has been concentrated and the triethylamine has been removed, 42 parts of colourless crystals are obtained which, after recrystallization from methanol, have a melting point of 104° to 105°C.

EXAMPLE 2

N-3,5-dichlorophenyl-5-methyl-5-(1-bromovinyl)-oxazolidinedione 5 parts of potassium tert-butylate is added to 30 parts of N-3,5-dichlorophenyl-5-(1,2-dibromoethyl)-oxazolidine-2,4-dione (m.p. 147° to 149°C) (obtained from N-3,5-dichlorophenyl-5-methyl-5-vinyloxazolidinedione by reaction with bromine) in 100 parts of benzene. The mixture is then stirred for 48 hours at room temperature. Concentration is carried out after removal of the salt and base. Colourless crystals are obtained having a melting point of 90° to 95°C (from hexane).

EXAMPLE 3

The active ingredients are added to a nutrient solution ideally suited for promoting the growth of the fungus Aspergillus niger in amounts of 100, 75, 50, 25, 10, 5 and 1 part(s) per million parts of nutrient solution. 20 ml of the nutrient solution prepared in this manner is placed in 100 ml Erlenmeyer flasks and inoculated with 0.3 mg of spores of Aspergillus niger. The flasks are heated for 120 hours at 36°C. The extent of fungus spread — predominantly on the surface of the solution — is subsequently assessed.

| Active ingredient | Amount of ingredient in nutrient solution in parts per million parts of solution | | | | | | |
|---|---|---|---|---|---|---|---|
| | 100 | 75 | 50 | 25 | 10 | 5 | 1 |
| 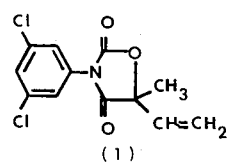 (1) | 0 | 0 | 0 | 0 | 0 | 2 | 5 |
| 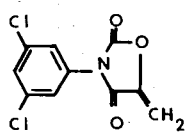 | 0 | 0 | 0 | 0 | 3 | 3 | 5 |
| 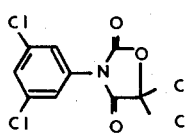 (2) (comparative agent) | 0 | 1 | 2 | 2 | 3 | 3 | 5 |
| control untreated) | 5 | 5 | 5 | 5 | 5 | 5 | 5 |

0 = no fungus growth, graduated down to
5 = uncontrolled fungus growth (surface of nutrient solution completely covered by fungus)

EXAMPLE 4

Leaves of barley seedlings grown in pots are sprayed with aqueous emulsions consisting of 80% active ingredient and 20% emulsifier. After the sprayed layer has dried the leaves are dusted with oidia of barley mildew (Erysiphe graminis var. hordei). The plants are subsequently placed in a greenhouse kept at from 20° to 22°C and having a relative humidity of 75 to 80%. The extent of fungus spread is assessed after 10 days.

| Active ingredient | Leaf attack after spraying with liquor containing active ingredient in amounts of | |
|---|---|---|
| | 0.2% | 0.1% |
| Compound 1 | 0 | 2 |
| Compound 2 (comparative agent) | 4 | 5 |
| Control (untreated) | 5 | |

0 = no attack, graduated down to
5 = total leaf area covered with fungus

EXAMPLE 5

Leaves of cucumber seedlings grown in pots are sprayed with aqueous emulsions consisting of 80% active ingredient and 20% emulsifier. After the sprayed layer has dried the leaves are dusted with oidia of cucumber mildew (Erysiphe cichoriacearum). The plants are subsequently placed in a greenhouse kept at from 20° to 22°C and having a relative humidity of 75 to 80%. The extent of fungus spread is assessed after 10 days.

| Active ingredient | Leaf attack after spraying with liquor containing active ingredient in amounts of | |
|---|---|---|
| | 0.2% | 0.1% |
| Compound 1 | 0 | 2 |
| Compound 2 (comparative agent) | 4 | 5 |
| Control (untreated) | 5 | |

0 = no attack, graduated down to
5 = total leaf area covered with fungus

EXAMPLE 6

90 parts by weight of compound 1 is mixed with 10 parts by weight of N-methyl-α-pyrrolidone. A mixture is obtained which is suitable for application in the form of very fine drops.

EXAMPLE 7

20 parts by weight of the compound of Example 2 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 8

20 parts by weight of the compound of Example 1 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02 % by weight of the active ingredient.

EXAMPLE 9

20 parts by weight of the compound of Example 2 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 10

20 parts by weight of the compound of Example 1 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 11

3 parts by weight of compound 1 is intimately mixed with 97 parts by weight of particulate kaolin. A dust is obtained containing 3% by weight of the active ingredient.

EXAMPLE 12

30 parts by weight of compound 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

We claim:
1. N-(3,5-dichlorophenyl)-5-methyl-5-vinyloxazolidine-2,4-dione.

* * * * *